(12) United States Patent
Nogami et al.

(10) Patent No.: US 10,517,495 B2
(45) Date of Patent: Dec. 31, 2019

(54) ELECTROCARDIOGRAM ANALYZER

(71) Applicants: UNIVERSITY OF TSUKUBA, Tsukuba-shi, Ibaraki (JP); NIHON KOHDEN CORPORATION, Shinjuku-ku, Tokyo (JP)

(72) Inventors: Akihiko Nogami, Tsukuba (JP); Koji Takizawa, Tokyo (JP)

(73) Assignees: UNIVERSITY OF TSUKUBA, Ibaraki (JP); NIHON KOHDEN CORPORATION, Tokyo (JP)

( * ) Notice: Subject to any disclaimer, the term of this patent is extended or adjusted under 35 U.S.C. 154(b) by 82 days.

(21) Appl. No.: 15/205,562

(22) Filed: Jul. 8, 2016

(65) Prior Publication Data

US 2017/0014042 A1    Jan. 19, 2017

(30) Foreign Application Priority Data

Jul. 14, 2015    (JP) .................. 2015-140573

(51) Int. Cl.
*A61B 5/04*    (2006.01)
*A61B 5/0432*    (2006.01)
(Continued)

(52) U.S. Cl.
CPC .......... *A61B 5/04012* (2013.01); *A61B 5/042* (2013.01); *A61B 5/044* (2013.01);
(Continued)

(58) Field of Classification Search
CPC . A61B 5/04012; A61B 5/04085; A61B 5/042; A61B 5/0422; A61B 5/0432;
(Continued)

(56) References Cited

U.S. PATENT DOCUMENTS

2009/0281441 A1    11/2009  Zhang et al.
2010/0268059 A1*   10/2010  Ryu .................. A61B 5/042
                                               600/407

(Continued)

FOREIGN PATENT DOCUMENTS

WO    9502995 A1    2/1995
WO    9510225 A1    4/1995
WO    9605768 A1    2/1996

OTHER PUBLICATIONS

Extended European Search Report dated Dec. 22, 2016, by the European Patent Office in counterpart European Application No. 16178933.4.

(Continued)

*Primary Examiner* — Carl H Layno
*Assistant Examiner* — Erin M Piateski
(74) *Attorney, Agent, or Firm* — Sughrue Mion, PLLC

(57) ABSTRACT

An electrocardiogram analyzer includes a first acquiring section that acquires a body surface electrocardiogram of a subject, a second acquiring section that acquires an intracardiac electrocardiogram of a ventricle of a heart of the subject, and an analyzing section that performs a frequency analysis on the intracardiac electrocardiogram and includes a range setting section that sets an analysis time range of the frequency analysis in the intracardiac electrocardiogram based on a unit waveform of the body surface electrocardiogram, and a calculating section that, in the analysis time range, performs the frequency analysis on the intracardiac electrocardiogram, and that calculates an index value indicating a ratio of local abnormal ventricular activities in the intracardiac electrocardiogram.

16 Claims, 9 Drawing Sheets

(51) Int. Cl.
*A61B 5/042* (2006.01)
*A61B 5/044* (2006.01)
*A61B 5/0408* (2006.01)
*A61B 5/00* (2006.01)
*A61B 5/0456* (2006.01)
*G16H 50/30* (2018.01)
*G16H 50/20* (2018.01)
*A61B 5/0428* (2006.01)

(52) U.S. Cl.
CPC .......... *A61B 5/0422* (2013.01); *A61B 5/0432* (2013.01); *A61B 5/0456* (2013.01); *A61B 5/04085* (2013.01); *A61B 5/7203* (2013.01); *A61B 5/7253* (2013.01); *A61B 5/7275* (2013.01); *G16H 50/20* (2018.01); *G16H 50/30* (2018.01); *A61B 5/0428* (2013.01); *A61B 5/6852* (2013.01); *A61B 5/7221* (2013.01); *A61B 2505/05* (2013.01)

(58) Field of Classification Search
CPC ..... A61B 5/044; A61B 5/0456; A61B 5/7203; A61B 5/7253; A61B 5/7275; A61B 5/0428; A61B 5/6852; A61B 5/7221; A61B 2505/05; G06F 19/3431; G06F 19/345
USPC ................................................ 600/517, 523
See application file for complete search history.

(56) References Cited

U.S. PATENT DOCUMENTS

| | | | |
|---|---|---|---|
| 2011/0196248 A1* | 8/2011 | Grunwald | A61B 5/04017 600/509 |
| 2013/0274623 A1* | 10/2013 | Zhang | A61B 5/04012 600/517 |
| 2016/0089048 A1* | 3/2016 | Brodnick | A61B 5/7246 600/512 |

OTHER PUBLICATIONS

Bieito Campos et al.; "Use of a novel fragmentation map to identify the substrate for ventricular tachycardia in postinfarction cardiomyopathy"; Heart Rhythm; vol. 12; No. 1; Oct. 2014; 9 pages total.

* cited by examiner

ELECTROCARDIOGRAM ANALYZER

CROSS REFERENCE TO RELATED APPLICATION

This application is based on Japanese Patent Applications No. 2015-140573 filed on Jul. 14, 2015, the contents of which are incorporated herein by reference.

BACKGROUND

The presently disclosed subject matter relates to an apparatus for analyzing an electrocardiogram acquired from a subject.

Usually, ventricular tachycardia means a condition where the heartbeat is different from the normal rhythm of the heart, and premature ventricular contraction occurs frequently in the ventricle. Ventricular tachycardia may cause worsening of heart failure, and sudden death, and therefore requires attention.

Conventionally, therefore, it is known that ventricular tachycardia is treated by selectively performing ablation on the abnormal site which causes ventricular tachycardia, by using a cardiac catheter. In order to perform the treatment, it is important to correctly identify the position where ablation is to be performed.

With respect to identification of the position of an abnormal site in the ventricle, it has been reported that, in a myocardium portion of the ventricle in which a substrate for ventricular tachycardia exists, high-frequency LAVA (Local Abnormal Ventricular Activities) are observed in addition to a sinus rhythm ventricular wave (V-wave). There is a non-patent Literature 1, Bieito Campos et al., "Use of Novel Fragmentation Map to Identify the Substrate for Ventricular Tachycardia in Post Infarction Cardiomyopathy," Heart Rhythm, 2014 October. The non-patent Literature 1 proposes an analysis technique in which a frequency analysis is performed on an intracardiac electrocardiogram of the ventricle, thereby quantitatively analyzing a ratio of LAVA contained in a sinus rhythm ventricular wave.

In an intracardiac electrocardiogram of the ventricle, however, LAVA sometimes appear after a sinus rhythm ventricular wave, and in other cases appears overlappingly with a ventricular wave. Moreover, an intracardiac electrocardiogram may contain noises due to the contact state of an electrode of a catheter, those caused by influences of myocardial sites which are remote from the measurement site (an atrial wave and a far-field potential), etc. In the case where a frequency analysis is to be performed on an intracardiac electrocardiogram of the ventricle as disclosed in Non-patent Literature 1, therefore, a medical person must adequately adjust and set an analysis time range of the frequency analysis while the shape of each unit waveform contained in the intracardiac electrocardiogram, and waveforms before and after the unit waveform are checked so that LAVA do not leak from the analysis time range. In the technique, in the case where points (mapping points) from which an electrocardiogram is to be acquired are as many as several hundreds, a process of setting the analysis time range takes a long time. Therefore, it is difficult to, during catheter treatment, identify the position of the abnormal site by a frequency analysis.

Therefore, it is an object of the presently disclosed subject matter to provide an electrocardiogram analyzer in which a frequency analysis can be performed on an intracardiac electrocardiogram of a ventricle in a manner easier than the conventional technique.

SUMMARY

According to an aspect of the presently disclosed subject matter, the electrocardiogram analyzer of the presently disclosed subject matter includes, a first acquiring section which acquires a body surface electrocardiogram of a subject, a second acquiring section which acquires an intracardiac electrocardiogram of a ventricle of a heart of the subject, and an analyzing section which performs a frequency analysis on the intracardiac electrocardiogram, and the analyzing section has a range setting section which sets an analysis time range of the frequency analysis in the intracardiac electrocardiogram based on a unit waveform of the body surface electrocardiogram, and a calculating section which, in the analysis time range, performs the frequency analysis on the intracardiac electrocardiogram, and which calculates an index value indicating a ratio of local abnormal ventricular activities (LAVA) in the intracardiac electrocardiogram.

A body surface electrocardiogram is less affected by noises than an intracardiac electrocardiogram, and in linkage with the sinus rhythm in an intracardiac electrocardiogram. According to the configuration, based on a unit waveform of a body surface electrocardiogram, therefore, the analysis time range in the intracardiac electrocardiogram of the ventricle can be set accurately and automatically so as to contain the potential variation of the measurement place in the ventricle and LAVA accompanying thereto. Then, also the index value indicating the ratio of LAVA with respect to the intracardiac electrocardiogram within the analysis time range is automatically calculated. Even during the process of measuring the intracardiac electrocardiogram of the ventricle through, for example, an electrode disposed in a catheter, therefore, the index value indicating the ratio of LAVA in the intracardiac electrocardiogram within the analysis time range is automatically calculated, and the position of the abnormal site in the ventricle can be identified. According to the configuration, a medical person can omit the work of setting the analysis time range of the frequency analysis, which is manually performed in the prior art, and perform the frequency analysis in a manner easier than the conventional technique.

According to the electrocardiogram analyzer of the presently disclosed subject matter, a frequency analysis can be performed on an intracardiac electrocardiogram of the ventricle in a manner easier than the conventional technique.

DETAILED DESCRIPTION OF EMBODIMENTS

Figure 1:
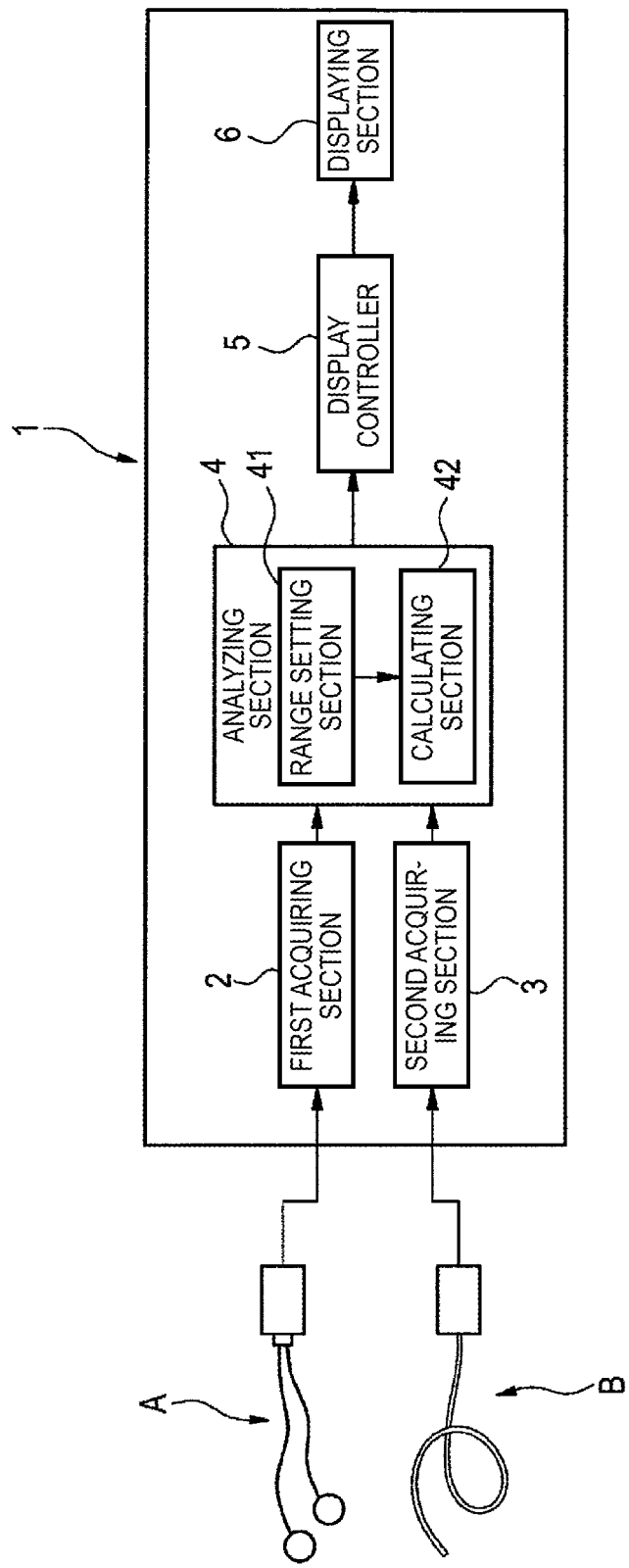
FIG. 1 is a diagram illustrating an electrocardiogram analyzer of an embodiment of the presently disclosed subject matter.

Hereinafter, an embodiment of the presently disclosed subject matter will be described in detail with reference to the drawings. FIG. 1 is a functional block diagram showing an electrocardiogram analyzer 1. The electrocardiogram analyzer 1 is an apparatus in which an abnormal site in the ventricle can be identified by performing a frequency analysis on an intracardiac electrocardiogram acquired from the ventricle of the heart of the subject. As illustrated in FIG. 1, the electrocardiogram analyzer 1 may include a first acquiring section 2, a second acquiring section 3, an analyzing section 4, a display controller 5, and a displaying section 6.

The first acquiring section 2 acquires a body surface electrocardiogram of the subject which is recorded by a recording unit A. The recording unit A is configured by, for example, electrodes for recording a standard 12-lead electrocardiogram, and the like.

The second acquiring section 3 acquires an intracardiac electrocardiogram of the subject which is recorded by a recording unit B. The recording unit B is configured by, for example, a cardiac catheter which is inserted into the heart through the vein to record an intracardiac electrocardiogram, and the like. As an intracardiac electrocardiogram, an intracardiac electrocardiogram in which a ventricular wave (V-wave) is recorded is used. An intracardiac electrocardiogram of the subject is recorded at a plurality of mapping points while moving the position of the electrode of the cardiac catheter.

Preferably, the first acquiring section 2 and the second acquiring section 3 are configured so that the timing when the first acquiring section 2 acquires a body surface electrocardiogram is synchronized with that when the second acquiring section 3 acquires an intracardiac electrocardiogram.

An analyzing section 4 performs a frequency analysis (for example, a fast Fourier transform) on the electrocardiogram by using the body surface electrocardiogram acquired by the first acquiring section 2, and the intracardiac electrocardiogram acquired by the second acquiring section 3. The analyzing section 4 may include a range setting section 41 and a calculating section 42.

The range setting section 41 sets an analysis time range where the frequency analysis is to be performed on the intracardiac electrocardiogram, based on each beat (hereinafter, referred to as a unit waveform) appearing in the body surface electrocardiogram. The analysis time range of the intracardiac electrocardiogram is set by means a predetermined period of time before and after, for example, the QRS waveform in each unit waveform of the body surface electrocardiogram. The QRS waveform means a waveform which is produced during ventricular activation.

The calculating section 42 performs the frequency analysis on the intracardiac electrocardiogram, in the analysis time range which is set by the range setting section 41. Moreover, the calculating section 42 calculates an index value for identifying an abnormal site in the ventricle, based on a result of the frequency analysis on the intracardiac electrocardiogram. The index value indicates the ratio of the LAVA (Local Abnormal Ventricular Activities) in the intracardiac electrocardiogram. The LAVA means a local abnormal potential which, in a sinus rhythm intracardiac electrocardiogram recorded in the ventricle, is fused (overlaps) with a potential variation of the ventricular wave or occurs separately from the potential variation of the ventricular wave.

The display controller 5 controls the contents to be displayed on the displaying section 6. Under control of the display controller 5, the displaying section 6 displays analysis information of the electrocardiogram which is supplied from the analyzing section 4. The displaying section 6 is configured by, for example, a touch panel liquid crystal display.

The operation principle of the electrocardiogram analyzer 1 will be described with reference to FIGS. 2A and 3B.

As a preparation step, the electrodes of the recording unit A are attached to the body surface (the four limbs, the chest, and the like) of the subject. The cardiac catheter of the recording unit B is inserted into the ventricle of the subject, and the electrode is indwelled at a mapping point. Each time when the electrocardiogram analysis at each mapping point has been ended, the position of the mapping point where the electrode of the cardiac catheter is to be indwelled is moved to the next mapping point.

Figure 2A:
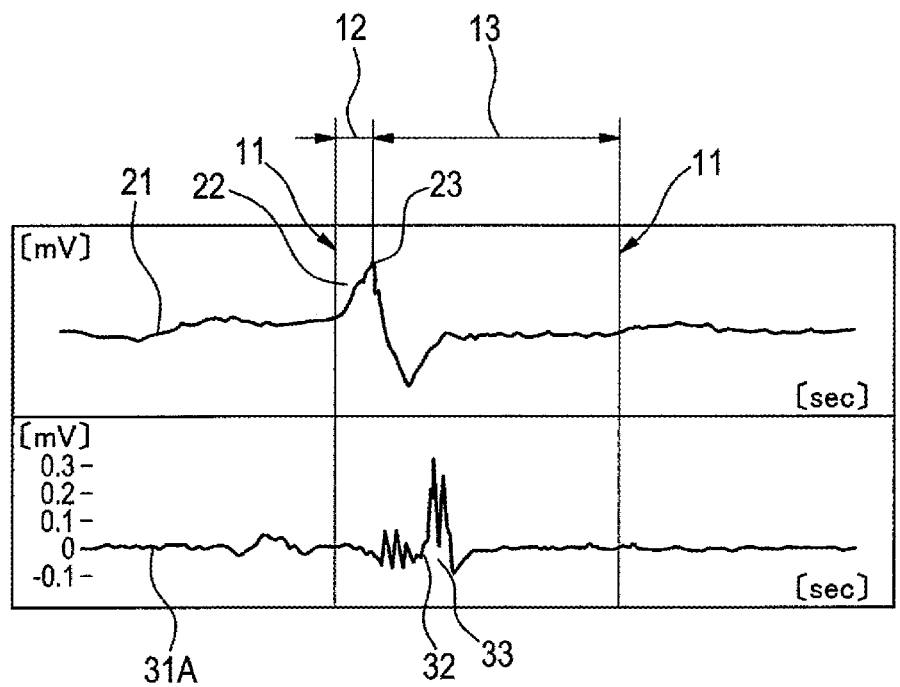
FIGS. 2A and 2B illustrates the operation principle of the analyzer.
Figure 3A:
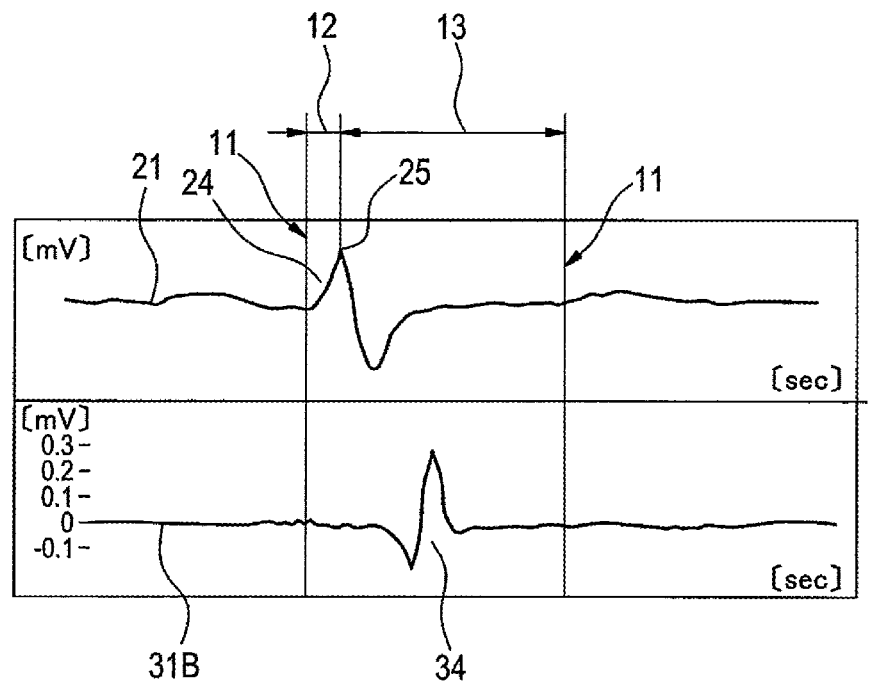
FIGS. 3A and 3B illustrates the operation principle of the analyzer.

When the operation of analyzing the electrocardiogram is started, as illustrated in the upper portions of FIGS. 2A and 3A, the body surface electrocardiogram 21 of the subject is recorded by the recording unit A. In synchronization with the timing of recording the body surface electrocardiogram 21, as illustrated in the lower portions of FIGS. 2A and 3A, intracardiac electrocardiograms 31A, 31B of the subject are recorded by the recording unit B. The intracardiac electrocardiograms 31A, 31B are intracardiac electrocardiograms which are recorded in different mapping points.

The intracardiac electrocardiogram 31A illustrated in FIG. 2A indicates an intracardiac electrocardiogram which is recorded while an abnormal site in the ventricle is set as the mapping point. By contrast, the intracardiac electrocardiogram 31B illustrated in FIG. 3A indicates an intracardiac electrocardiogram which is recorded while a normal myocardium site in the ventricle is set as the mapping point. In a myocardium site (abnormal site) in which a substrate for ventricular tachycardia exists, LAVA may sometimes occur in an intracardiac electrocardiogram during a sinus rhythm. The intracardiac electrocardiogram 31A indicates an intracardiac electrocardiogram which occurs as a result of fusion of LAVA 33 with a potential variation of a ventricular wave 32. By contrast, the intracardiac electrocardiogram 31B indicates an intracardiac electrocardiogram in which LAVA do not occur and only a potential variation of a ventricular wave 34 is recorded.

LAVA sometimes occur after a position where a potential variation of the ventricular wave occurs, while separating from the ventricular wave, or in other cases, as indicated in the intracardiac electrocardiogram 31A, occur while fusing with a potential variation of the ventricular wave. Surrounding noises are easily superimposed on an intracardiac electrocardiogram. In the case where LAVA occur while fusing with a potential variation of the ventricular wave, therefore, it is difficult to visually check LAVA, and hence an occurrence of LAVA is often overlooked.

Therefore, the inventors have focused attention on the phenomenon in which the frequency components of LAVA contain a larger amount of high-frequency components than those of a potential variation of the ventricular wave, and studied a method in which a frequency analysis is performed on an intracardiac electrocardiogram to detect an occurrence of LAVA.

In this case, it is important to set an analysis time range where the frequency analysis is to be performed, so as to contain at least LAVA. In the embodiment, when the analysis time range is to be set, an R wave peak in the body surface electrocardiogram is used as a reference point.

In FIG. 2A, an area designating line 11 which surrounds an area in a rectangular shape indicates the analysis time range. The analysis time range 11 is configured by a front period 12 which is in front of the peak 23 of the R-wave in the body surface electrocardiogram 21, and a rear period 13 which is in rear of the peak. The front period 12 is set so as to contain the Q-wave which indicates the starting timing of ventricular contraction. The rear period 13 is set to a period which can include LAVA that occurs after the ventricular wave while separating from the ventricular wave. Specifically, the rear period is set to a period which is in front of the P-wave that indicates the timing when the atrium starts the next operation. The periods are previously set by the operator through an input operating section. The range setting section 41 detects the peak 23 of the R-wave in a unit waveform 22 of the body surface electrocardiogram 21, and sets the front period 12 and rear period 13 with respect to the detected peak 23, as the analysis time range 11 of the intracardiac electrocardiogram 31A.

Also in FIG. 3A, the analysis time range 11 is set in a same or similar manner. The range setting section 41 detects the peak 25 of the R-wave in a unit waveform 24 of the body surface electrocardiogram 21, and sets the front period 12 and rear period 13 with respect to the detected peak 25, as the analysis time range 11 of the intracardiac electrocardiogram 31B.

The calculating section 42 performs the frequency analysis on the intracardiac electrocardiograms 31A, 31B in the preset analysis time range 11.

Figure 2B:
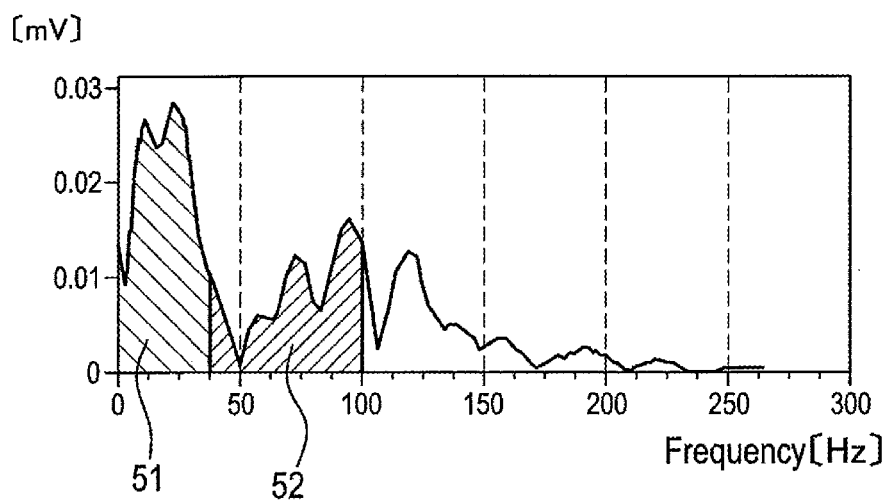
Figure 3B:
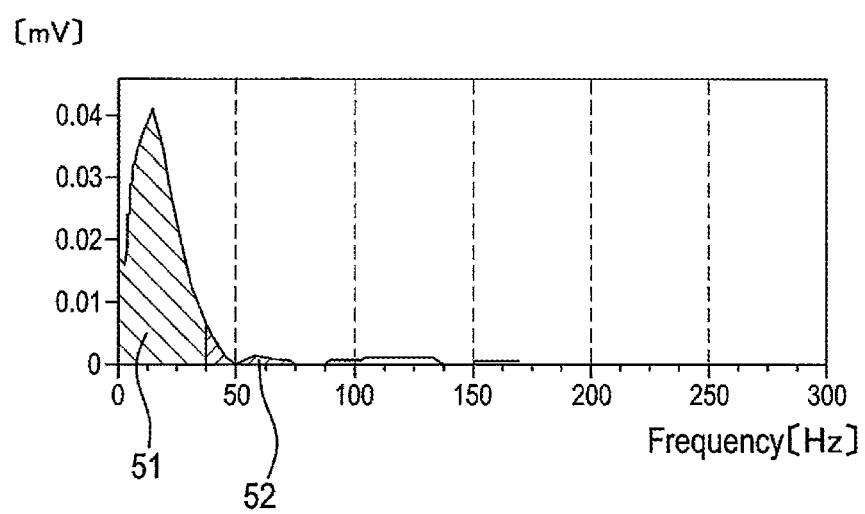

FIG. 2B illustrates the frequency distribution in the analysis time range 11 of the intracardiac electrocardiogram 31A (see FIG. 2A), and FIG. 3B illustrates the frequency distribution in the analysis time range 11 of the intracardiac electrocardiogram 31B (see FIG. 3A). When comparing the two frequency distributions with each other, it is seen that the frequency distribution (FIG. 2B) of the intracardiac electrocardiogram 31A in which LAVA 33 are fused with the potential variation of the ventricular wave 32 contains a larger amount of high-frequency components than the frequency distribution (FIG. 3B) of the intracardiac electrocardiogram 31B in which only the potential variation of the ventricular wave 34 exists (LAVA do not occur).

The calculating section 42 calculates the ratio of predetermined frequency components (in the example, 40 to 100 Hz) contained in a certain range (in the example, 1 to 100 Hz) of the frequency distribution, as an AR (Area Ratio). For example, the area ratio AR can be indicated by following Exp. 1:

$$AR = Area[40 \text{ to } 100 \text{ Hz}] / Area[1 \text{ to } 100 \text{ Hz}] \quad \text{(Exp. 1)}.$$

Exp. 1 shows the ratio of the frequency distribution amount of 40 to 100 Hz with respect to that of 1 to 100 Hz. In FIGS. 2B and 3B, this indicates the area ratio of the hatched area 52 with respect to the hatched area (51+52). The AR value is defined as a ratio of LAVA contained in the analysis time range of the intracardiac electrocardiogram, and used as an index value for identifying an abnormal site in the ventricle.

Figure 4:
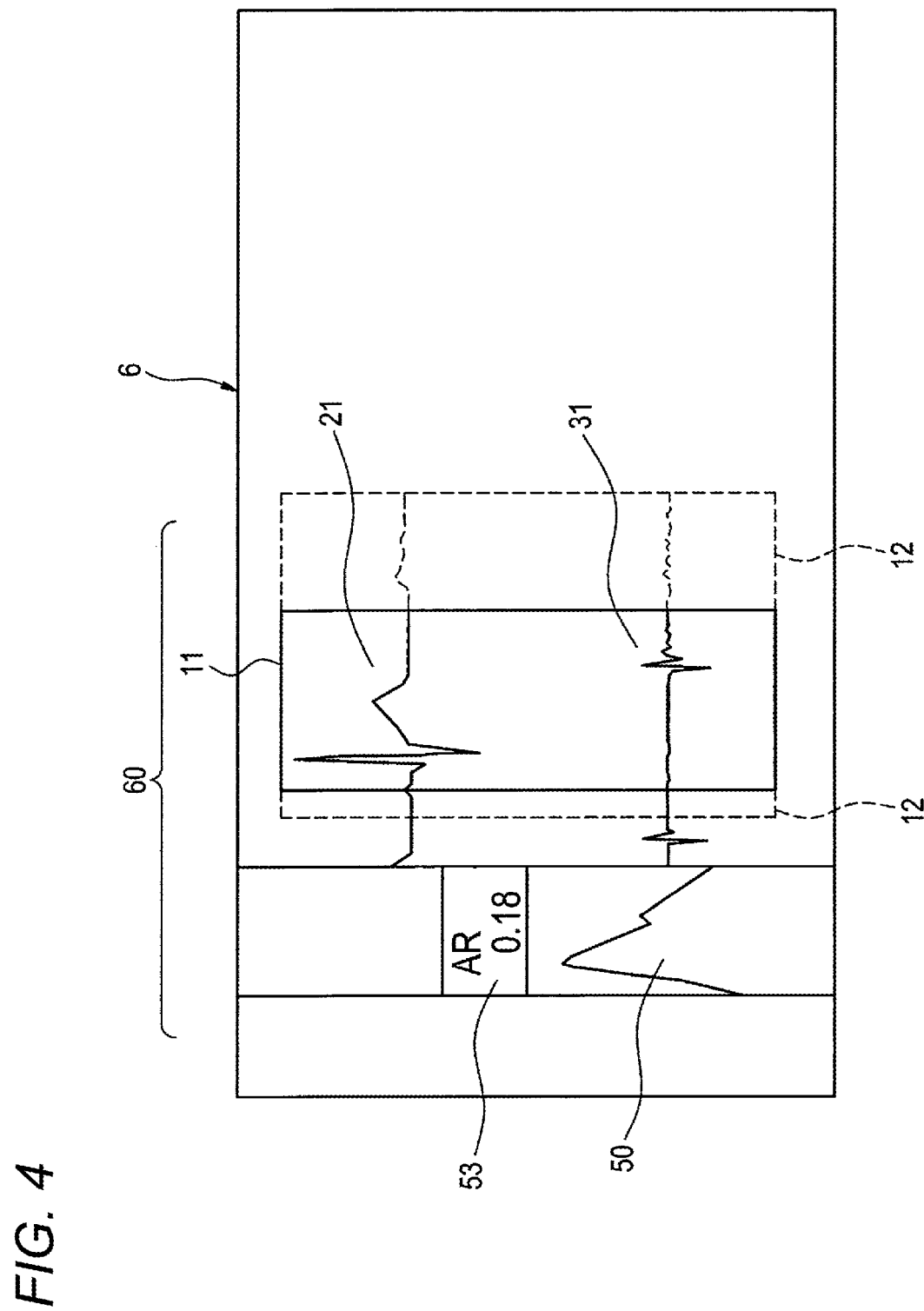
FIG. 4 illustrates a display example of a displaying section disposed in the analyzer.

As illustrated in FIG. 4, electrocardiogram analysis information 60 which is analyzed in the electrocardiogram analyzer 1 is displayed on the displaying section 6. The electrocardiogram analysis information 60 includes, for example, the body surface electrocardiogram 21, the intracardiac electrocardiogram 31, the frequency distribution 50, the AR value (index value) 53, and the like. The body surface electrocardiogram 21 and the intracardiac electrocardiogram 31 which is recorded in synchronization with the body surface electrocardiogram 21 are displayed, for example, in a vertically juxtaposed manner. The body surface electrocardiogram 21 and the intracardiac electrocardiogram 31 are sequentially displayed in each unit waveform. The displaying section is configured so that the timing of switching the display of each unit waveform can be arbitrarily set. For example, the switching may be performed at each time when a peak of the R wave is detected, in order to display all unit waveforms, or every several seconds. The analysis time range 11 indicating the ranges where the frequency analysis is to be performed is displayed on the body surface electrocardiogram 21 and the intracardiac electrocardiogram 31. On the left side of the body surface electrocardiogram 21 and the intracardiac electrocardiogram 31, for example, the frequency distribution 50 and AR value 53 which are obtained by performing frequency analyzation on the analysis time range 11 of the intracardiac electrocardiogram 31 are juxtaposedly displayed. The frequency distribution 50 and the AR value 53 are set so that they are acquired at each time when the unit waveform is detected, and their display is switched in synchronization with the display switching timing of the unit waveform.

According to the configuration, the QRS waveform of the body surface electrocardiogram is used for setting the analysis time range of the frequency analysis in the intracardiac electrocardiogram. A body surface electrocardiogram is less affected by noises than an intracardiac electrocardiogram, and in linkage with the sinus rhythm in an intracardiac electrocardiogram. Based on the unit waveform 22 of the body surface electrocardiogram, therefore, the analysis time range in the intracardiac electrocardiograms 31A, 31B of the ventricle can be set accurately and automatically so as to contain the potential variations of the ventricular waves 32, 34 at mapping points of the ventricle, and LAVA which occur (accompany thereto) while fusing with or separating from them. Moreover, a frequency analysis is performed on the intracardiac electrocardiograms 31A, 31B in the thus set analysis time range 11, whereby also the AR value (index value) indicating the ratio of the LAVA 33 to the intracardiac electrocardiograms 31A, 31B can be automatically calculated. Even during the process of recording the intracardiac electrocardiograms 31A, 31B of the ventricle through the electrode of the cardiac catheter, therefore, the AR value indicating the ratio of the LAVA 33 in the intracardiac electrocardiograms 31A, 31B within the analysis time range 11 can be automatically calculated, and the position of the abnormal site in the ventricle can be identified in a short time. A medical person can omit the work of setting the analysis time range of the frequency analysis, which is manually performed in prior art, and perform the frequency analysis on an intracardiac electrocardiogram of the ventricle in a manner easier than the conventional technique.

Moreover, the body surface electrocardiogram 21 and intracardiac electrocardiograms 31A, 31B which are recorded from the subject are acquired in synchronization with each other by the electrocardiogram analyzer 1. Therefore, the analysis time range 11 in which the linkage between the electrocardiograms is considered can be easily set, and the analysis time range 11 can be set further accurately.

As indicated by the broken lines 12 in FIG. 4, the analysis time range 11 in which the frequency analysis is to be performed in the intracardiac electrocardiogram 31 can be configured so as to be adjusted based on an operation by the operator. The analysis time range 11 can be adjusted by, for example, touch-operating operation buttons (not shown) displayed on the displaying section 6. In this case, the frequency distribution 50 and the AR value 53 are again analyzed and calculated in accordance with the adjustment of the analysis time range 11, and then updated.

According to the configuration, the analysis time range 11 can be adequately adjusted in accordance with the features of the acquired electrocardiogram waveforms. Therefore, the frequency analysis can be performed more accurately, and the position of an abnormal site in the ventricle can be accurately identified.

Figure 5:
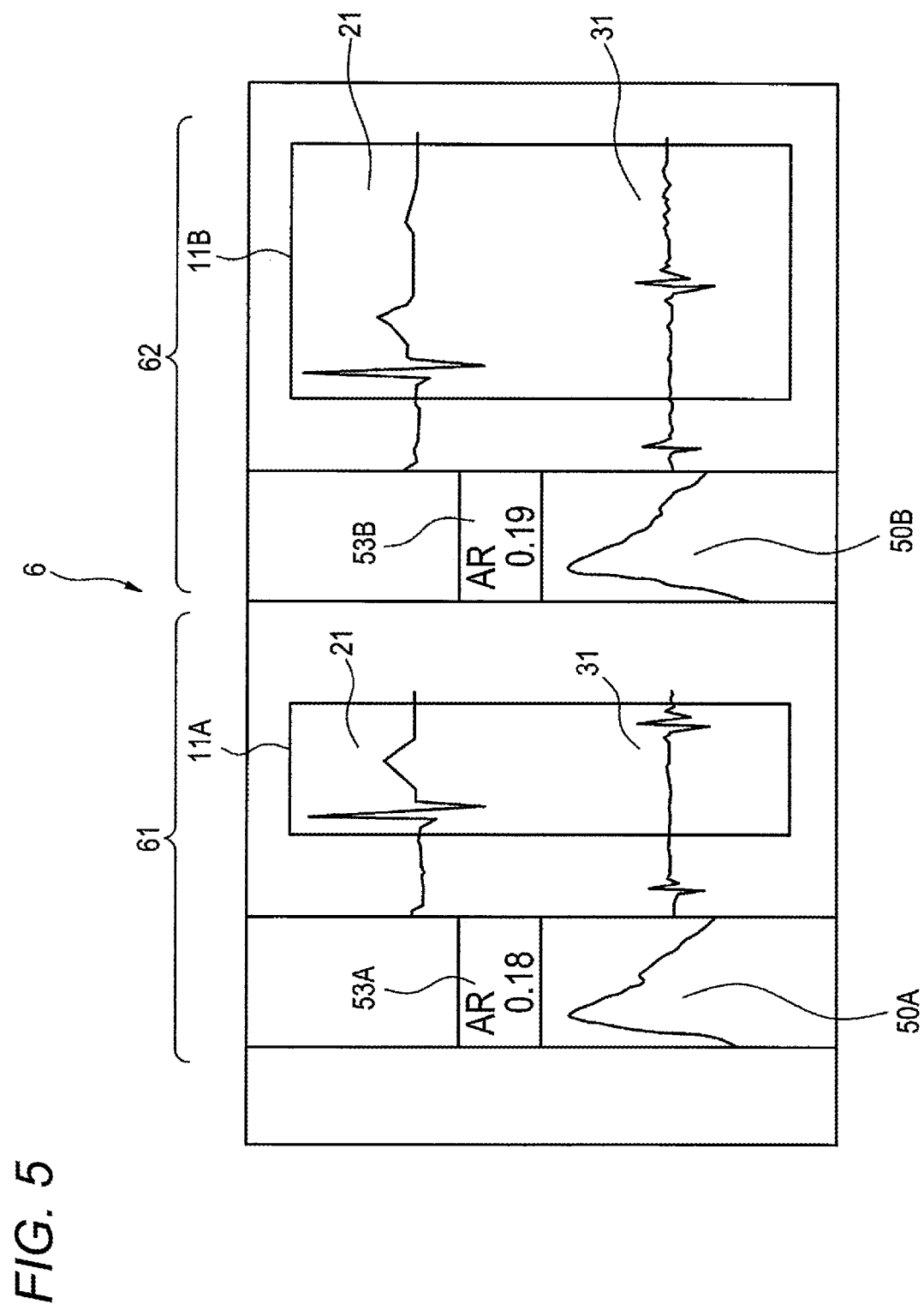
FIG. 5 illustrates another display example displayed on the displaying section.

As illustrated in FIG. 5, the plural (in the example, two) sets of electrocardiogram analysis information 61, 62 which are analyzed by the electrocardiogram analyzer 1 may be simultaneously displayed on the displaying section 6. In the case where the analysis time range where the frequency analysis is to be performed in the intracardiac electrocardiogram 31 is adjusted by an operation by the operator, for example, the sets of electrocardiogram analysis information 61, 62 in analysis time ranges 11A, 11B before and after the adjustment can be simultaneously displayed in a juxtaposed manner on the displaying section 6. The switching to this screen can be performed by, for example, touch-operating operation buttons (not shown) displayed on the displaying section 6.

According to the configuration, AR values 53A, 53B before and after the adjustment of the analysis time range are simultaneously displayed. Therefore, an adequate analysis time range can be selected while comparing results (AR values) of a plurality of adjustments with one another, and the frequency analysis can be performed more accurately.

Figure 6:
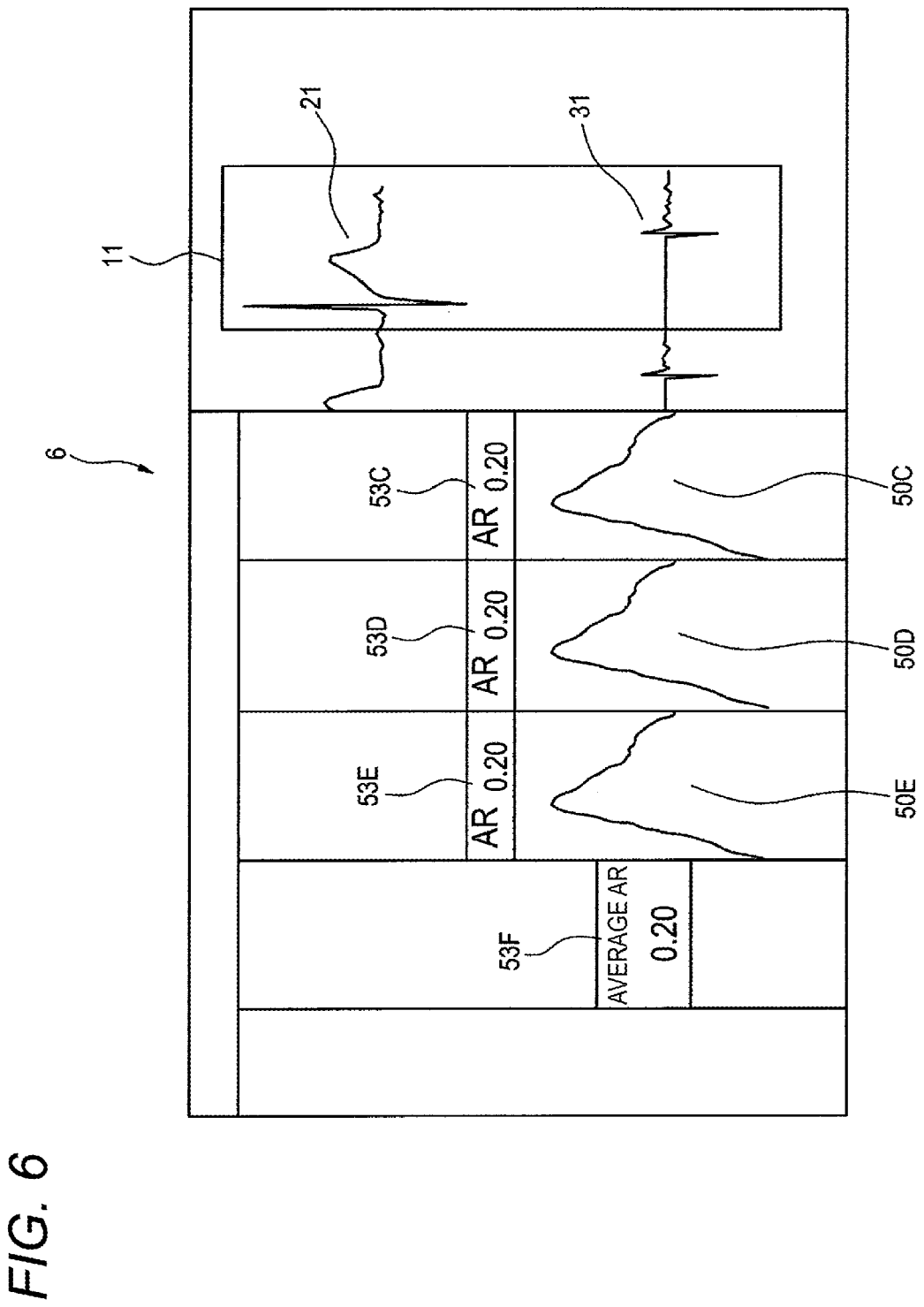
FIG. 6 illustrates a further display example displayed on the displaying section.

As illustrated in FIG. 6, AR values 53C, 53D, 53E which are calculated with respect to a plurality (in the example, three) of successive unit waveforms, respectively may be simultaneously displayed on the displaying section 6. Among the three frequency distributions and AR values which are juxtaposedly displayed on the displaying section 6, the frequency distribution 50C and the AR value 53C indicate electrocardiogram analysis information which is obtained with respect to unit waveforms of the body surface electrocardiogram 21 and intracardiac electrocardiogram 31 that are currently displayed. The frequency distribution 50D and the AR value 53D indicate electrocardiogram analysis information which is obtained with respect to unit waveforms of one beat earlier, and the frequency distribution 50E and the AR value 53E indicate electrocardiogram analysis information which is obtained with respect to unit waveforms of two beats earlier. The average AR value 53F indicate electrocardiogram analysis information which is obtained by averaging the AR values 53C, 53D, 53E. The switching to this screen can be performed by touch-operating operation buttons in a similar manner as described above.

According to the configuration, since the AR values which are successively calculated are compared with each other, it is possible to confirm whether an intracardiac electrocardiogram of the subject is acquired in a stabilized state or not.

Figure 7:
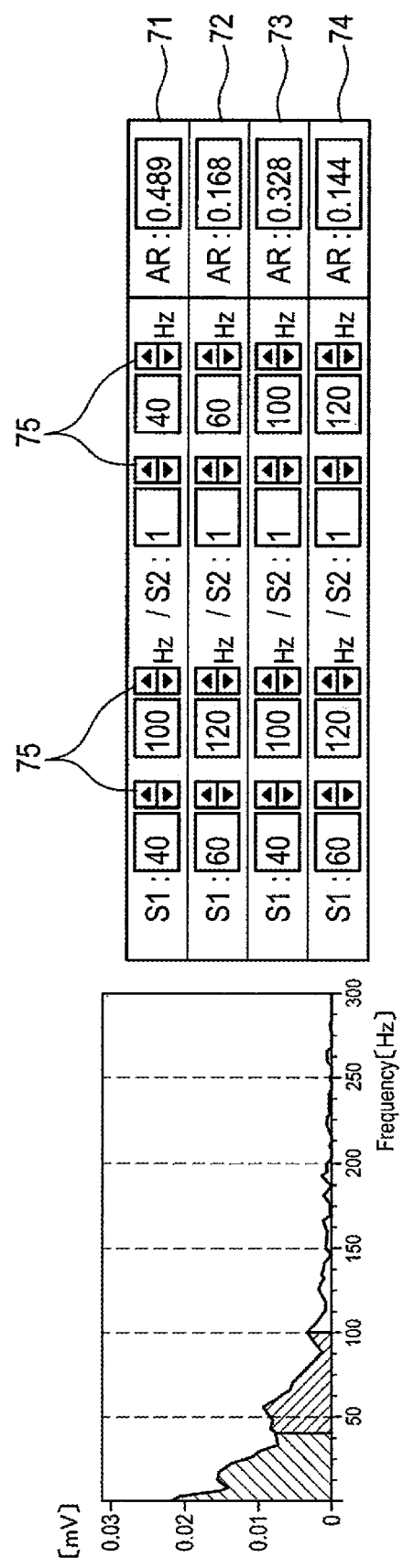
FIG. 7 illustrates an example a frequency range which is used in calculation of an index value by the analyzer.

As illustrated in FIG. 7, the frequency range of the predetermined area which is used for calculating the AR value can be arbitrarily set. In the above-described calculation of (Exp. 1), for example, the frequency ranges indicated by S1 and S2 of a setting example 73 in FIG. 7 are used. In (Exp. 1) above, namely, the frequency range of the numerator is set to 40 to 100 Hz, and that of the denominator is set to 1 to 100 Hz. These frequency ranges can be changed by operating setting buttons 75 to arbitrary frequency ranges such as setting examples 71, 72, 74. The preset plural frequency ranges (setting examples 71 to 74) can be simultaneously displayed together with the calculated AR values on the displaying section 6. The operator can select the frequency range to be used, from the displayed setting examples 71 to 74. The switching to this screen can be performed by touch-operating operation buttons in a similar manner as described above.

According to the configuration, even in the case where frequency components of LAVA are dispersed, when the frequency range is changed to an adequate range, it is possible to calculate an appropriate AR value. Therefore, the position of an abnormal site in the ventricle can be identified more accurately. Moreover, AR values in a plurality of frequency ranges which are arbitrarily set can be simultaneously displayed on the displaying section 6. Therefore, an adequate frequency range can be selected while comparing the values with one another, and the position of an abnormal site can be identified more accurately.

Figure 8:
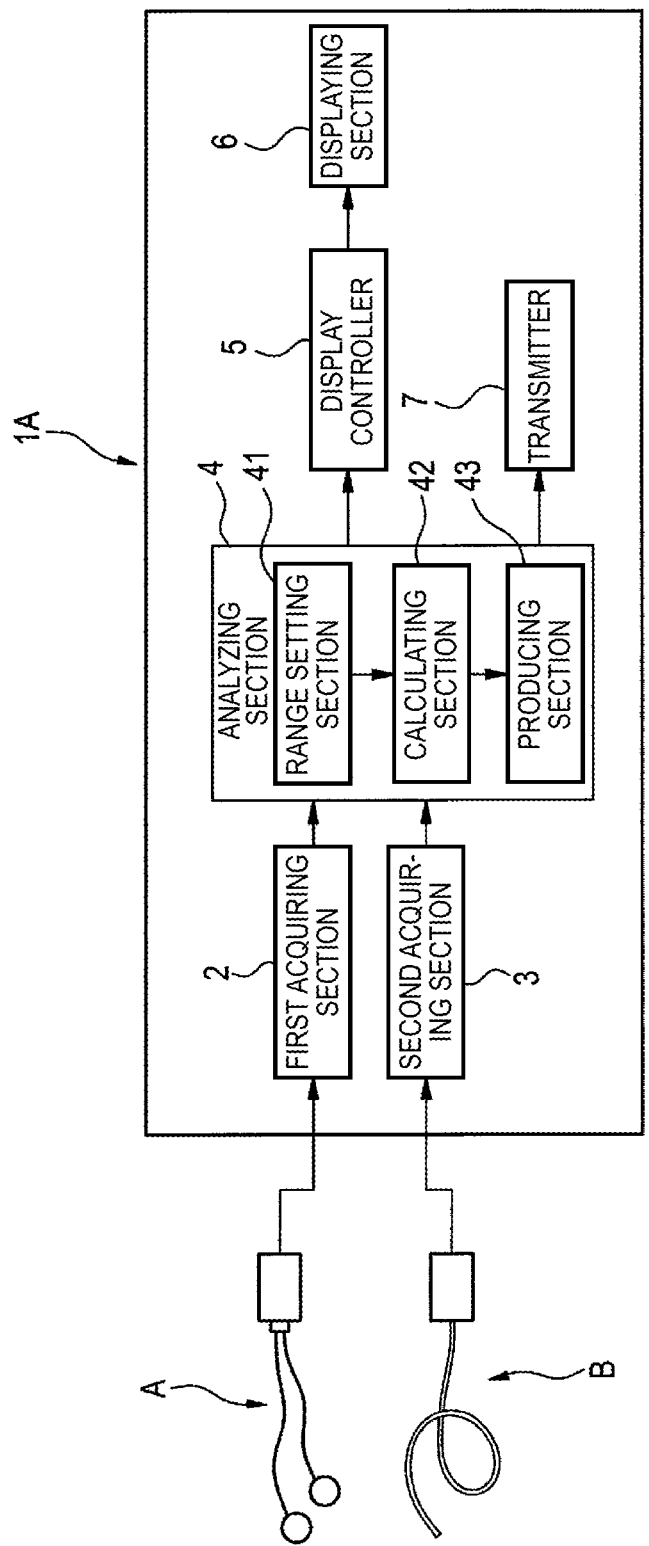
FIG. 8 illustrates an example of the configuration of the analyzer.
Figure 9:
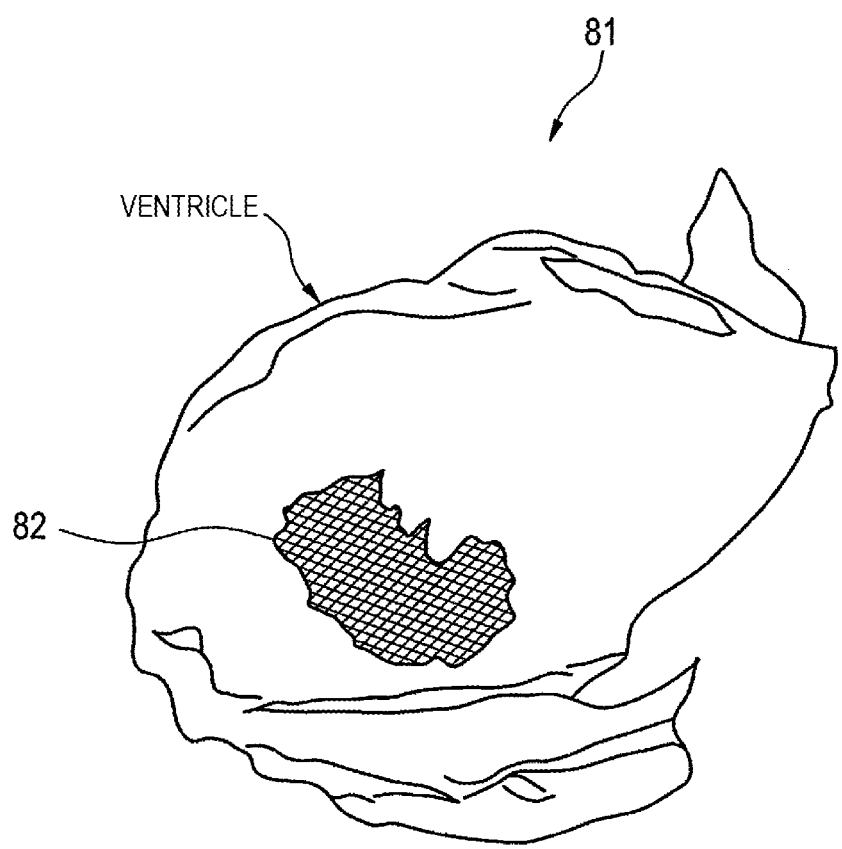
FIG. 9 illustrates a visualized result of an analysis performed by the analyzer.

As illustrated in FIG. 8, an electrocardiogram analyzer 1A may include a producing section 43. The producing section 43 is disposed in, for example, the analyzing section 4, and, based on the AR value calculated by the calculating section 42, determines whether the mapping point (measurement site) of the ventricle is an abnormal site or not. The AR value indicates the contained ratio of LAVA in the analysis time range of the intracardiac electrocardiogram. Therefore, in the case where the AR value exceeds a preset threshold, for example, it is determined that the mapping point is an abnormal site. Based on the position data of the mapping point and the result of the determination of the AR value, the producing section 43 produces visualization data for visually discriminating normal and abnormal sites in the ventricle from each other. The visualization data are configured by color data for displaying normal and abnormal sites in different display modes (for example, different colors or patterns). Based on the visualization data, the display controller 5 may cause a 3D map 81 such as illustrated in FIG. 9 to be displayed on the displaying section 6. In the example, in the 3D map 81, a site indicated by the cross-hatching lines 82 is illustrated as an abnormal site.

As illustrated in FIG. 8, the electrocardiogram analyzer 1A may include a transmitter 7. The transmitter 7 transmits the visualization data produced by the producing section 43, to an external 3D mapping apparatus. In this case, the transmitter 7 is configured so as to transmit the visualization data each time when the mapping point is moved in the ventricle and the AR value for the mapping point is calculated. Based on the transmitted visualization data, the 3D mapping apparatus may display the 3D map 81 such as illustrated in FIG. 9.

According to the configuration, a medical person or the like can visually check the position of an abnormal site, and perform, for example, ablation by using the catheter. During treatment, the AR value can be quickly reflected in the 3D mapping apparatus, and a substrate for tachycardia can be identified from the whole map. This can be useful to ablation treatment.

The above-described embodiment is a mere example for facilitating understanding of the presently disclosed subject matter, and does not limit the presently disclosed subject matter. It is obvious that the embodiment may be adequately changed or improved without departing the spirit of the presently disclosed subject matter, and equivalents are included within the scope of the presently disclosed subject matter.

What is claimed is:

1. An electrocardiogram analyzer comprising:
a processor configured to receive a body surface electrocardiogram of a subject, receive an intracardiac electrocardiogram of a ventricle of a heart of the subject, perform a frequency analysis on the intracardiac electrocardiogram, set a reference point as an R wave peak in the body surface electrocardiogram based on a unit waveform of the body surface electrocardiogram, set an analysis time range of the frequency analysis in the intracardiac electrocardiogram based on a starting timing of ventricular contraction before the R wave peak and a timing of next operation of an atrium after the R wave peak and, in the analysis time range, perform the frequency analysis on the intracardiac electrocardiogram, and calculate an index value indicating a ratio of local abnormal ventricular activities in the intracardiac electrocardiogram.

2. The electrocardiogram analyzer according to claim 1, wherein the analysis time range which is set is adjustable based on an operation by an operator.

3. The electrocardiogram analyzer according to claim 2, further comprising:
a display; and
a display controller that controls display contents of the display,
wherein the display controller causes a plurality of index values which are based on the analysis time range that has been adjusted by the operator, to be simultaneously displayed on the display.

4. The electrocardiogram analyzer according to claim 1, further comprising:
a display; and
a display controller that controls display contents of the display,
wherein the display controller causes a plurality of index values which are successively calculated, to be simultaneously displayed on the display.

5. The electrocardiogram analyzer according to claim 1, wherein the processor is further configured to:
determine whether a measurement site of a ventricle is an abnormal site or not, based on the index value, and produce visualization data for displaying the abnormal site in a display mode that is different from a display mode of a normal site.

6. The electrocardiogram analyzer according to claim 2, wherein the processor is further configured to:
determine whether a measurement site of a ventricle is an abnormal site or not, based on the index value, and produce visualization data for displaying the abnormal site in a display mode that is different from a display mode of a normal site.

7. The electrocardiogram analyzer according to claim 3, wherein the processor is further configured to:
determine whether a measurement site of a ventricle is an abnormal site or not, based on the index value, and produce visualization data for displaying the abnormal site in a display mode that is different from a display mode of a normal site.

8. The electrocardiogram analyzer according to claim 4, wherein the processor is further configured to:
determine whether a measurement site of a ventricle is an abnormal site or not, based on the index value, and produce visualization data for displaying the abnormal site in a display mode that is different from a display mode of a normal site.

9. The electrocardiogram analyzer according to claim 1, wherein a timing of acquiring the body surface electrocardiogram is synchronized with a timing of acquiring the intracardiac electrocardiogram.

10. The electrocardiogram analyzer according to claim 2, wherein a timing of acquiring the body surface electrocardiogram is synchronized with a timing of acquiring the intracardiac electrocardiogram.

11. The electrocardiogram analyzer according to claim 3, wherein a timing of acquiring the body surface electrocardiogram is synchronized with a timing of acquiring the intracardiac electrocardiogram.

12. The electrocardiogram analyzer according to claim 4, wherein a timing of acquiring the body surface electrocardiogram is synchronized with a timing of acquiring the intracardiac electrocardiogram.

13. The electrocardiogram analyzer according to claim 5, wherein a timing of acquiring the body surface electrocardiogram is synchronized with a timing of acquiring the intracardiac electrocardiogram.

14. The electrocardiogram analyzer according to claim 6, wherein a timing of acquiring the body surface electrocardiogram is synchronized with a timing of acquiring the intracardiac electrocardiogram.

15. The electrocardiogram analyzer according to claim 7, wherein a timing of acquiring the body surface electrocardiogram is synchronized with a timing of acquiring the intracardiac electrocardiogram.

16. The electrocardiogram analyzer according to claim 8, wherein a timing of acquiring the body surface electrocardiogram is synchronized with a timing of acquiring the intracardiac electrocardiogram.

* * * * *